(12) United States Patent
Fleury et al.

(10) Patent No.: US 6,918,894 B2
(45) Date of Patent: *Jul. 19, 2005

(54) HUBER NEEDLE WITH ANTI-REBOUND SAFETY MECHANISM

(75) Inventors: Michael T. Fleury, Portage, WI (US); Fergie F. Ferguson, Brea, CA (US); Dongchul D. Hyun, Brea, CA (US)

(73) Assignee: Medical Product Specialists, Brea, CA (US)

( * ) Notice: Subject to any disclaimer, the term of this patent is extended or adjusted under 35 U.S.C. 154(b) by 81 days.

This patent is subject to a terminal disclaimer.

(21) Appl. No.: 10/375,963

(22) Filed: Feb. 28, 2003

(65) Prior Publication Data

US 2003/0163098 A1 Aug. 28, 2003

Related U.S. Application Data

(60) Provisional application No. 60/360,406, filed on Feb. 28, 2002.

(51) Int. Cl.[7] ................................................. A61M 5/32
(52) U.S. Cl. ........................ 604/272; 604/174; 604/198; 128/919
(58) Field of Search ............................ 604/93.01, 110, 604/116, 117, 162, 164.04, 164.07, 164.08, 165.01, 165.02, 165.03, 165.04, 174, 177, 192, 197, 198, 263, 264, 272; 128/919

(56) References Cited

U.S. PATENT DOCUMENTS

| | | | |
|---|---|---|---|
| 3,924,617 A | 12/1975 | Ferro | |
| 4,411,657 A | 10/1983 | Galindo | |
| 4,413,993 A | 11/1983 | Guttman | |
| 4,675,006 A | 6/1987 | Hrushesky | |
| 4,753,641 A | 6/1988 | Vaslow | |
| 4,755,173 A | 7/1988 | Konopka | |
| 4,772,272 A | 9/1988 | McFarland | |
| 4,795,432 A | 1/1989 | Karczmer | |
| 4,804,371 A | 2/1989 | Vaillancourt | |
| 4,906,236 A | 3/1990 | Alberts et al. | |
| 4,929,237 A | 5/1990 | Medway | |
| 4,990,135 A | 2/1991 | Truesdale, Jr. | |
| 5,015,240 A | 5/1991 | Soproni et al. | |
| RE34,045 E | 8/1992 | McFarland | |
| 5,135,504 A | 8/1992 | McLees | |
| 5,176,650 A | 1/1993 | Haining | |
| 5,176,656 A | 1/1993 | Bayless | |
| 5,254,106 A | 10/1993 | Feaster | |
| 5,267,974 A | 12/1993 | Lambert | |
| 5,328,482 A | 7/1994 | Sircom et al. | |

(Continued)

Primary Examiner—Nicholas D. Lucchesi
Assistant Examiner—Mark K. Han
(74) Attorney, Agent, or Firm—Stetina Brunda Garred & Brucker (57) ABSTRACT

A safety needle device for protecting a user against a needle-stick injury. This needle device includes a needle housing having a distal housing opening. A needle is disposed within the needle housing and has a distal needle portion which extends away therefrom through the distal housing opening. An elongate sheath assembly surrounds the needle within the needle housing. A trigger member retains the sheath assembly within the needle housing against a force urging the sheath assembly towards the distal housing opening. The trigger member is sized and configured to release the sheath assembly from retention to allow the sheath assembly to transition towards and out of the distal housing opening via the force. This causes the sheath assembly to enclose the distal needle portion and protect the user against the needle stick injury.

21 Claims, 10 Drawing Sheets

U.S. PATENT DOCUMENTS

| | | | |
|---|---|---|---|
| 5,364,362 A | 11/1994 | Schulz | |
| 5,403,283 A | 4/1995 | Luther | |
| D365,630 S | 12/1995 | Sullivan | |
| 5,478,238 A | 12/1995 | Gourton et al. | |
| 5,520,654 A | 5/1996 | Walhberg | |
| 5,591,138 A * | 1/1997 | Vaillancourt | 604/198 |
| 5,611,781 A | 3/1997 | Sircom et al. | |
| 5,662,619 A | 9/1997 | Zarate | |
| 5,702,369 A | 12/1997 | Mercerau | |
| 5,713,874 A | 2/1998 | Ferber | |
| 5,725,503 A | 3/1998 | Arnett | |
| 5,746,215 A | 5/1998 | Manjarrez | |
| 5,755,699 A | 5/1998 | Blecher et al. | |
| 5,795,336 A | 8/1998 | Romano et al. | |
| 5,817,058 A | 10/1998 | Shaw | |
| 5,846,227 A | 12/1998 | Osterlind | |
| 5,848,996 A | 12/1998 | Eldor | |
| 5,851,196 A | 12/1998 | Arnett | |
| 5,879,330 A | 3/1999 | Bell | |
| 5,891,098 A | 4/1999 | Huang | |
| 5,893,845 A | 4/1999 | Newby et al. | |
| 5,951,512 A | 9/1999 | Dalton | |
| 5,951,522 A | 9/1999 | Rosato et al. | |
| 5,964,739 A | 10/1999 | Champ | |
| 5,984,899 A * | 11/1999 | D'Alessio et al. | 604/198 |
| 5,997,504 A | 12/1999 | Bell | |
| 6,120,492 A | 9/2000 | Finch et al. | |
| 6,165,157 A | 12/2000 | Dillon et al. | |
| 6,186,179 B1 | 2/2001 | Hill | |
| 6,210,371 B1 | 4/2001 | Shaw | |
| 6,238,375 B1 | 5/2001 | Powell | |
| 6,241,710 B1 | 6/2001 | Van Tassel et al. | |
| 6,261,259 B1 | 7/2001 | Bell | |
| 6,261,264 B1 | 7/2001 | Tamaro | |
| 6,261,272 B1 | 7/2001 | Gross et al. | |
| 6,280,420 B1 | 8/2001 | Ferguson et al. | |
| 6,280,424 B1 | 8/2001 | Chang et al. | |
| 6,290,682 B1 | 9/2001 | Myers | |
| 6,322,537 B1 | 11/2001 | Chang | |
| 6,346,096 B1 | 2/2002 | Yam et al. | |
| 6,355,021 B1 | 3/2002 | Neilsen et al. | |
| 6,659,983 B2 * | 12/2003 | Crawford et al. | 604/192 |
| 2001/0039401 A1 | 11/2001 | Ferguson et al. | |
| 2002/0010434 A1 | 1/2002 | Larsen et al. | |
| 2002/0072716 A1 | 6/2002 | Barrus et al. | |

* cited by examiner

HUBER NEEDLE WITH ANTI-REBOUND SAFETY MECHANISM

CROSS-REFERENCE TO RELATED APPLICATIONS

The present application is a continuation-in-part of U.S. patent application Ser. No. unknown entitled "HUBER NEEDLE WITH ANTI-REBOUND SAFETY MECHANISM" filed Jan. 24, 2003, which claims the benefit of U.S. Provisional Application No. 60/360,406 entitled "HUBER NEEDLE WITH ANTI-REBOUND MECHANISM" filed Feb. 28, 2002, the entirety of the disclosures of which are expressly incorporated herein by reference.

STATEMENT RE: FEDERALLY SPONSORED RESEARCH/DEVELOPMENT (Not Applicable)

BACKGROUND OF THE INVENTION

The present invention relates generally to medical needle devices, and more particularly to an improved, passive safety needle device featuring a sheath assembly which is designed to be outwardly deployable and enclose the exposed portion of an affixed needle therewithin so as to protect its user against inadvertent needle-stick injuries.

Needle-stick injuries are common and are of great concern in today's health-care industry. A vast majority of these injuries occur while withdrawing conventional Huber needles from implanted IV ports after administering medicants such as antibiotics or chemotherapy.

More specifically, a great deal of force is required during Huber needle withdrawal to overcome the resistance of the port's septum. Since a non-dominant hand is typically used in this process to secure the implanted port, it often becomes stuck on the rebound of the Huber needle.

Because a Huber needle is utilized for venous access, such needle-stick injury as described above presents a high risk for pathogen transmission. An exposed and/or injured health-care worker must be tested for various blood-borne pathogens such as hepatitis B, hepatitis C and HIV.

Such testing is usually repeated to ensure that the exposed and/or injured health-care worker is not infected of those pathogens. As a further precaution, boosting of immunity may simultaneously take place as an additional insurance of safety.

In order to alleviate the dangers associated with needle-stick injuries, some health-care workers have fashioned home-made guards to protect their non-dominant hands. However, these home-made guards are not user-friendly as the health-care workers must make the conscious choice to wear them every time an injection is made.

The health-care workers may sometimes neglect to put them on because they are either inconvenient to use, interfere with the process of administering the Huber needle or the health-care workers may just simply forget to wear them. All of these factors contribute to negating the guards' effectiveness to protect the health-care workers against the dangers of needle-stick injuries.

In view of the above-described shortcomings of conventional needle guards, there exists a need in the art for a safety needle guard which can protect health-care workers against the dangers of needle-stick injuries in a convenient and user-friendly manner. More specifically, there exists a need for a safety needle guard which can be automatically implemented in a user passive manner during the needle injection process so as to consistently protect the health-care workers against the dangers of needle-stick injuries.

BRIEF SUMMARY OF THE INVENTION

The present invention specifically addresses and alleviates the above-referenced deficiencies associated with the use of the Huber needle guards of the prior art. More particularly, the present invention is an improved, passive safety needle device featuring a sheath assembly which is outwardly deployable relative to the exposed portion of its affixed needle. By such deployment, a physical barrier can be placed around the needle by the sheath assembly to protect a user from being inadvertently stuck by the needle, thus preventing needle-stick injuries and all the risks that are associated with them. Although this sheath assembly is intended to be used for Huber needle applications, it is specifically recognized herein that such sheath assembly may be used in conjunction with other types of conventional needle applications as well.

In accordance with a preferred embodiment of the present invention, there is provided a passive safety needle device for protecting its user against a needle-stick injury. The safety needle device of the present invention first features a needle housing comprised of two substantially identical housing halves engaged to each other about their respective inner housing faces. Although such housing halves may be engaged in any manner or fashion, it is preferred that such engagement occurs through ultrasonic welding. Moreover, each of the two housing halves are preferably fabricated from a plastic material such as through the process of plastic injection molding.

The needle housing includes an internal groove which is elongated therewithin and communicates with its distal opening. This groove is preferably elongated in a manner as to substantially correspond to (i.e., be complementary to) the general arcuate curvature of the needle housing's, upper surface. In this respect, the internal groove defines a bend radius which is complementary in shape to the upper housing surface.

In the preferred embodiment of the present invention, the needle housing further includes a needle, of which its intermediate portion is disposed within the elongated groove. In this regard, that portion of the needle is formed in an arcuate configuration to match the bend radius of the groove so it can be accommodated therewithin. The needle utilized with the present needle device is preferably a stainless steel Huber needle having a non-coring distal needle point.

The needle defines a proximal needle portion which becomes exposed outside of the needle housing by extending through the needle housing's proximal opening. Flexible infusion tubing preferably made from silicone rubber and/or polyvinyl chloride or polyethylene surrounds this exposed proximal portion of the needle and connects to the needle housing through its proximal opening. The infusion tube or tubing can be maintained in this position by the engagement of the two housing halves which compress on the tubing.

A distal portion of the needle is defined generally opposite to the proximal needle portion. The needle portion is retained outside of the needle housing as it is extended downward through the distal housing opening. The distal needle portion forms a needle point at its exposed end which is used for penetrating the patient's skin and accessing the implanted port.

In the preferred embodiment, the needle housing has a lower housing surface that defines a lower housing recess.

This recess is primarily intended for accommodating a hold-down platform. The hold-down platform may be engaged within the recess through a variety attachment procedures such as adhesive or fastener. By providing platform strips which radially extend outward from such location of engagement, the hold-down platform may be placed near the injection point and be used for securing the safety needle device upon the patient by means of taping over the platform strips and the patient's skin. Preferably, the hold-down platform has a generally circular or rectangular configuration, and is fabricated from either a rubber or plastic material.

In accordance with a preferred embodiment of the present invention, an elongate sheath assembly is provided within the needle housing. More specifically, this sheath assembly is situated within the groove when disposed in a retracted position surrounding the intermediate portion of the needle. The sheath assembly has an axial length that is substantially identical to that of the elongated groove. Although the sheath assembly may be formed from various materials, it is preferably formed as an elongate wound stainless steel wire tube and/or semi-rigid polymer such as polyethylene or Teflon.

The sheath assembly of the preferred embodiment defines a distal sheath end. Attached to this end is a distal tip component which preferably comprises a transparent plastic tip. The tip component can be either insert molded or adhered to the distal sheath end. The distal tip component forms a distal tip having a diameter which is generally greater than that of the groove but substantially equal to or less than the diameter of the distal housing opening.

The sheath assembly further defines a proximal sheath end generally opposite to the distal sheath end. Attached to the proximal sheath end is a proximal tip component having a diameter which is generally greater than the diameter of the groove's distal opening. As will be discussed more fully below, such configuration allows the sheath assembly to stop once reaching the fully extended position, that is, the distal tip component being advanced over and beyond the distal needle point while enclosing the distal needle portion with the sheath assembly. Although other types of tip components may be contemplated, the proximal tip component utilized with the present invention is preferably formed as a stainless steel or plastic ferrule.

In the preferred embodiment of the present invention, a biasing member is provided within the needle housing. This biasing member is used for passively moving the sheath assembly along the groove between the retracted and extended positions. The biasing member is connected between the proximal tip component and a knob member disposed on the exterior of the needle housing.

The knob member allows the user to control the movement of the sheath assembly along the elongated groove. This is possible due to the mechanical connections with the proximal tip component of the sheath assembly and the biasing member. Because the preferred biasing member comprises a torsional biasing member which is configured to naturally urge the sheath assembly towards the extended position, the user may utilize the knob member to control the sheath assembly when moving along that direction. In the preferred embodiment, the biasing member comprises either a torsional arm or torsional spring. However, other types of biasing members are contemplated as they may also achieve the ultimate objective of passively deploying the sheath assembly outwardly with respect to the distal needle portion.

In accordance with an alternately preferred embodiment of the present invention, a passive safety needle device of modified structure is disclosed herein. This specific safety needle device is essentially designed to perform the same function as that of the above-described needle device through the use of a modified structural configuration. More specifically, it utilizes a different type of proximal tip component at the proximal sheath end for moving the sheath assembly along the groove.

In lieu of using a ferrule as the proximal tip component, the alternately configured needle device comprises a tip body which is preferably fabricated through plastic molding. Although other forms of attachment are contemplated herein, the tip body is preferably barb fitted through the proximal sheath end of the sheath assembly. This enables the tip body to be fixedly secured to the sheath assembly which allows it to transition along the groove when the tip body is urged by the biasing member (e.g., torsion spring) to move therealong.

The tip body is releasibly mounted upon a trigger member which is structurally configured to be elongated from within the needle housing to the outside thereof. In particular, the tip body is designed to maintain the sheath assembly in the retracted position against the force of the biasing member. To accomplish this, the trigger member extends a tip retaining projection through the tip body from its end which is disposed within the needle housing. Its opposite end is exposed through the needle housing and serves as a trigger mechanism for passively moving the tip body, and hence the sheath assembly, from the retracted position to the extended position. More particularly, the trigger member maintains the tip body and the sheath assembly in the retracted position until the tip body is manually released from the tip retaining projection. Such release of the tip body is performed by pressing the exposed end of the trigger member towards the needle housing. This causes the tip retaining projection to slip out from the tip body and free the tip body from its holding. Due to its connection with the biasing member which applies force towards the extended position, the tip body is automatically caused thereby to be moved in that direction, hence effectuating the same directional movement of the sheath assembly as well.

Similar to the above-described proximal tip component, the tip body possesses a body size which is substantially larger than the distal opening of the groove. This allows the tip body to stop once reaching and abutting the portion of the groove forming the narrowed distal opening. Upon reaching such positioning, the sheath assembly should now be deployed outside of the needle housing and be extended over the entirety of the needle's distal portion, including its tip. The sheath assembly is projected to remain outwardly deployed since the spring force applied by the biasing member would urge the tip body against the converged portion of the groove which forms its distal opening.

The operation of the safety needle device of the first embodiment is described herein to illustrate the operation of the safety needle device of the second embodiment as well. The safety needle device of the first embodiment is designed to protect a user from inadvertent needle stick during withdrawal of the needle from the patient. More specifically, the distal needle point is first injected into a designated skin area of the patient to access the implanted IV port. By such penetration, various tasks such as delivering fluids and medications, drawing blood for diagnostic testing and/or infusing blood products may be conducted. Optionally, the needle device can be secured in place by taping its platform strips to the patient's surrounding skin area.

After performing any one of the tasks as described above, the needle is withdrawn from the patient. While withdrawing the needle, the sheath assembly is deployed outwardly and passively from within the needle device relative to the distal needle portion resulting in the distal needle portion being completely enclosed and/or surrounded by the outwardly deployed sheath assembly. Such process can be facilitated by using the externally located knob member which allows the user to control the outward deployment of the sheath assembly. In the case of the second embodied safety needle device, the trigger member can be manually pressed inward to automatically trigger the outward deployment of the sheath assembly.

The needle device is then ready for proper disposal in a Sharps container or other container designated for used medical devices.

BRIEF DESCRIPTION OF THE DRAWINGS

These as well as other features of the present invention will become more apparent upon reference to the drawings wherein.

DETAILED DESCRIPTION OF THE INVENTION

Figure 1:
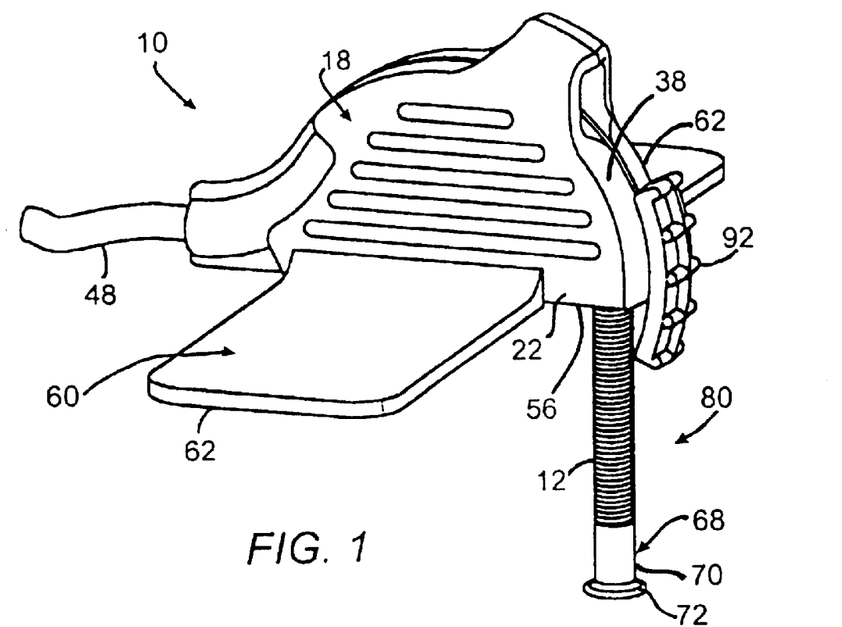
FIG. 1 is a perspective view of a safety needle device constructed in accordance with a preferred embodiment of the present invention and illustrating its needle housing having generally rectangular platform strips radially extending outward therefrom.

Referring now to the drawings wherein the showings are for purposes of illustrating preferred embodiments of the present invention only, and not for purposes of limiting the same, FIG. 1 illustrates a passive safety needle device 10 constructed in accordance with a preferred embodiment of the present invention. As indicated above, the present safety needle device 10 features a sheath assembly 12 which is outwardly deployable with respect to the distal needle portion 14, that is, the exposed portion of its affixed needle 16 which is used to access an IV port implanted underneath a patient's designated skin area (not shown).

As will be soon discussed, such passive deployment of the sheath assembly 12 provides a tangible physical barrier around the distal needle portion 14 to protect a user from being inadvertently stuck by the needle 16, thereby preventing needle-stick injuries and all the risks associated therewith. Although the sheath assembly 12 is preferably used for Huber needle applications, it is expressly contemplated herein that such sheath assembly 12 may be used for other types of conventional needle applications as well.

Referring more particularly to FIGS. 1 and 9a–9c, the safety needle device 10 includes a needle housing 18. Although this needle housing 18 may be formed from a unitary construction, it is preferably constructed from two substantially identical housing halves 20, 22 which are assembled to each other about their respective inner housing faces 24. The first housing half 20 includes at least one peg 26 that can be retained within at least one corresponding aperture (not shown) provided on the second housing half 22. The permanent engagement between the two housing halves 20, 22 is preferably accomplished with adhesive or ultrasonic welding or snap fit engagement.

The two substantially identical housing halves 20, 22 may be fabricated from any rigid material. However, the material of choice is a polymer (i.e., plastic). In this respect, the manufacture of each housing half 20 or 22 may be greatly expedited through utilizing the process of plastic injection molding techniques.

Figure 9A:
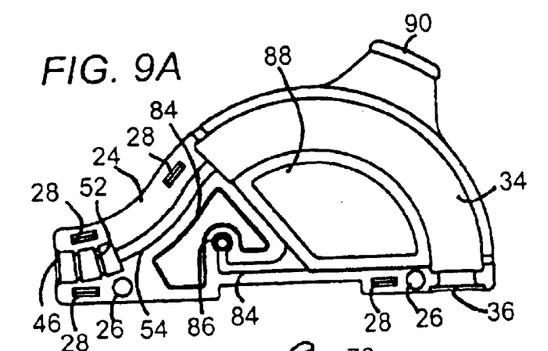
FIG. 9a is a side view of one housing half which is used to form the needle housing of FIG. 1 when engaged with the other housing half.
Figures 9B, 9C:
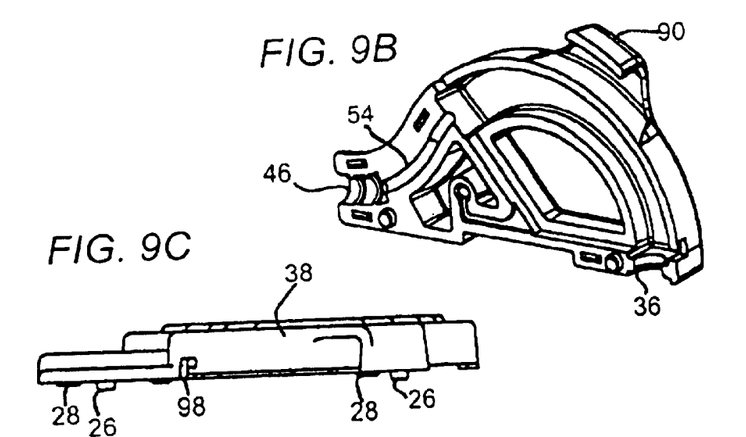
FIG. 9b is a perspective view of the housing half of FIG. 9a illustrating pegs formed about an inner housing face thereof.
FIG. 9c is a top view of the housing half of FIG. 9a illustrating its upper housing surface forming a proximal notch.
Figure 9D:
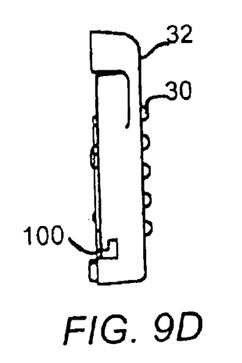
FIG. 9d is a rear view of the housing half of FIG. 9a illustrating its side housing surface forming finger-graspable projections.
Figure 11:
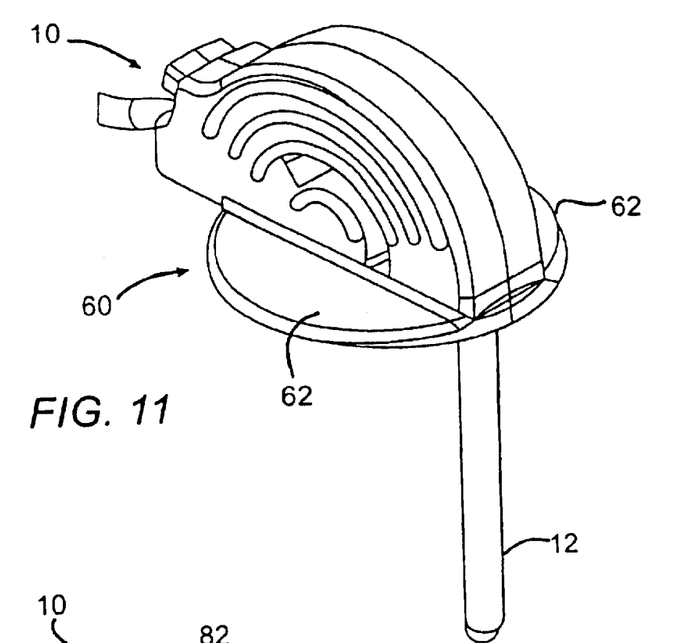
FIG. 11 is a perspective view of the safety needle device of FIG. 1 and illustrating its needle housing which uses generally half-circular platform strips as an alternative to the generally rectangular platform strips.
Figure 12:
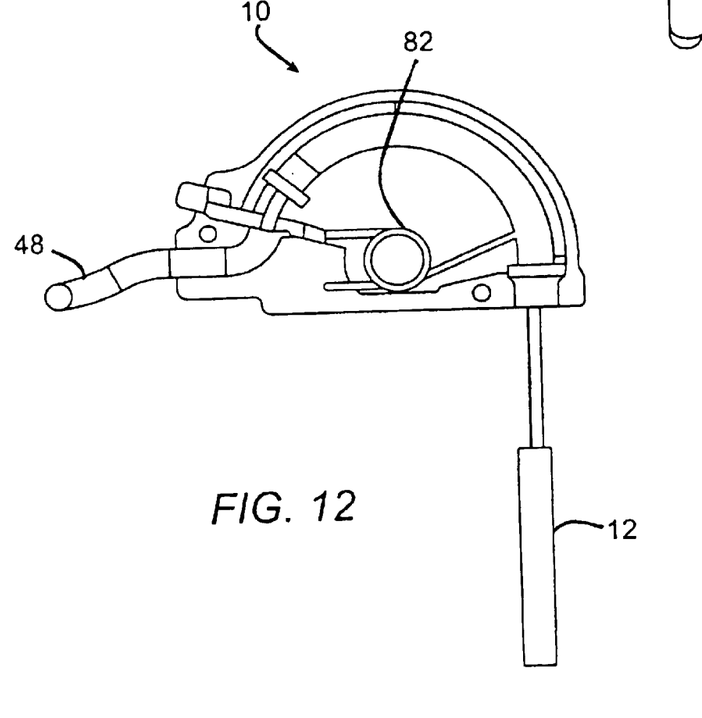
FIG. 12 is a side cross-sectional view of the safety needle device of FIG. 11 illustrating the use of a torsional spring as an alternative to the torsional arm.

Referring now to FIGS. 9d and 11, the exterior of the needle housing 18 preferably includes plural projections 30 to ease in the handling of the present safety needle device 10. These projections 30 may be formed on one or both sides 32 of the needle housing 18. As can be seen from the specified figures, the finger-graspable projections 30 may be provided as a group of linearly configured projections (as shown in FIG. 9d) or arcuately configured projections (as shown in FIG. 11).

Figure 2:
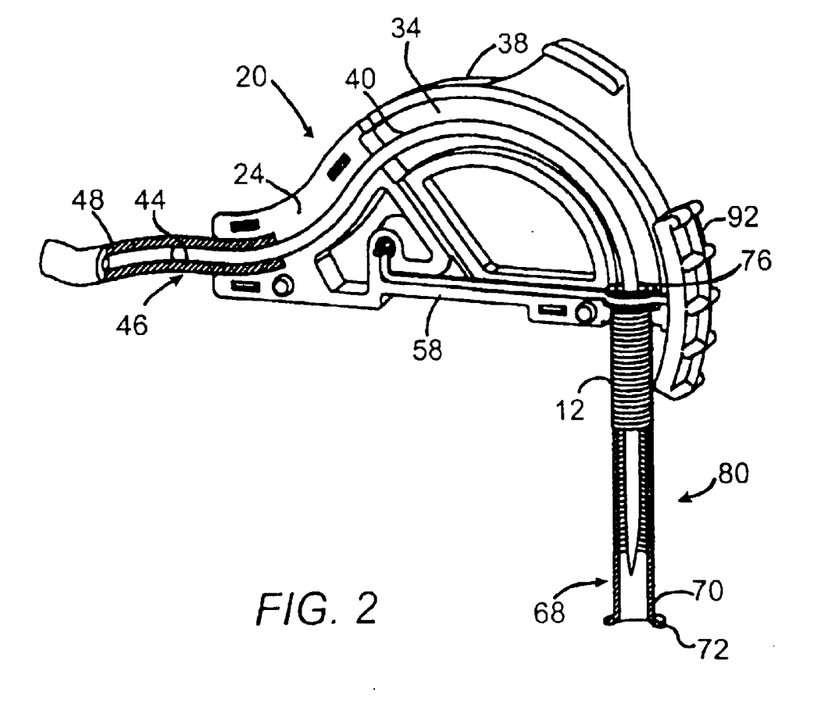
FIG. 2 is a perspective cross-sectional view of the safety needle device of FIG. 1 and illustrating the manner in which a sheath assembly is extended from within its needle housing.
Figure 4:
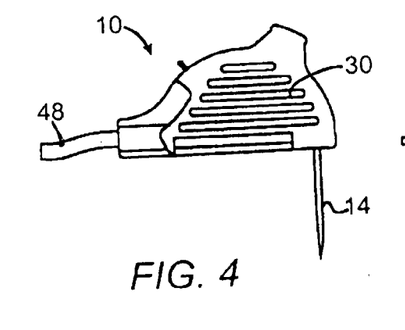
FIG. 4 is a side view of the safety needle device of FIG. 1 and illustrating a needle's exposed distal portion which extends downward out of its needle housing.
Figure 5A:
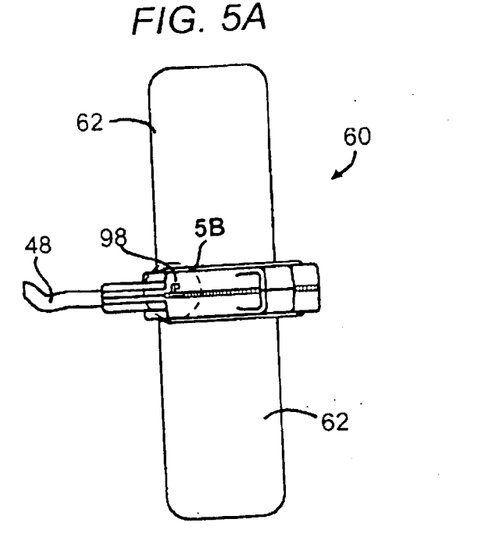
FIG. 5a is a top view of the safety needle device of FIG. 1 illustrating the flexible infusion tubing which is connected through a proximal opening of its needle housing.
Figure 5B:
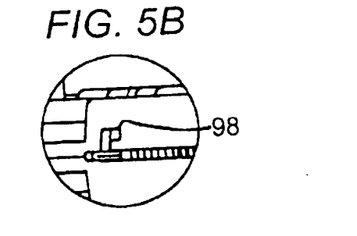
FIG. 5b is an enlarged view of the encircled portion of FIG. 5a, illustrating a proximal notch which is used for retaining a sheath assembly in a retracted position.
Figure 6A:
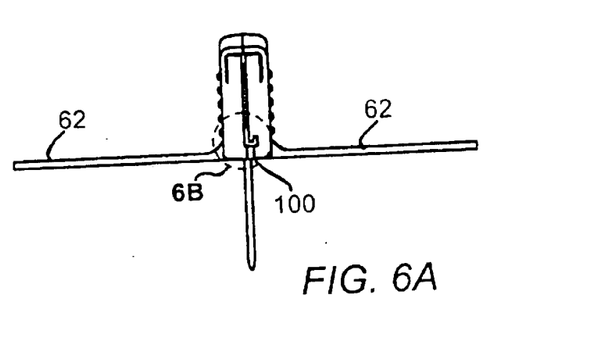
FIG. 6a is a front view of the safety needle device of FIG. 1 illustrating a needle's distal portion which is disposed generally perpendicular to the radially extending platform strips.
Figure 6B:
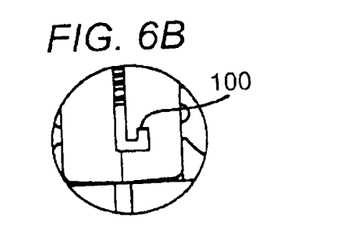
FIG. 6b is an enlarged view of the encircled portion of FIG. 6a, illustrating a distal notch which is used for securing a sheath assembly in an extended position.

As shown in FIGS. 2 and 4, the needle housing 18 includes an internal arcuate groove 34 which initiates intermediate the housing and extends to a distal opening 36 of the needle housing 18. Preferably, the groove 34 is formed in a generally complementary configuration to the general arcuate curvature of the needle housing's upper surface 38. As such, the internal groove 34 has a bend radius which closely simulates the bend radius of the upper housing surface 38.

The needle housing also contains a needle 16, of which an intermediate portion 40 thereof is disposed within the elongated groove 34. The intermediate needle portion 40 is sufficiently formed (i.e., bent to closely match the bend radius of the internal groove 34 so as to be accommodatingly disposed therewithin). The needle 16 preferably used with the present safety needle device 10 comprises a stainless steel Huber needle. However, other types of needles such as a conventional hypodermic syringe needle may be workable with the present safety needle device 10. Preferably, the needle 16 has a needle point 42 which is non-coring but use of the coring needle point may be contemplated. Of course, the needle point 42 is intended for penetrating a designated area of the patient's skin and accessing an IV port implanted underneath.

Figure 3:
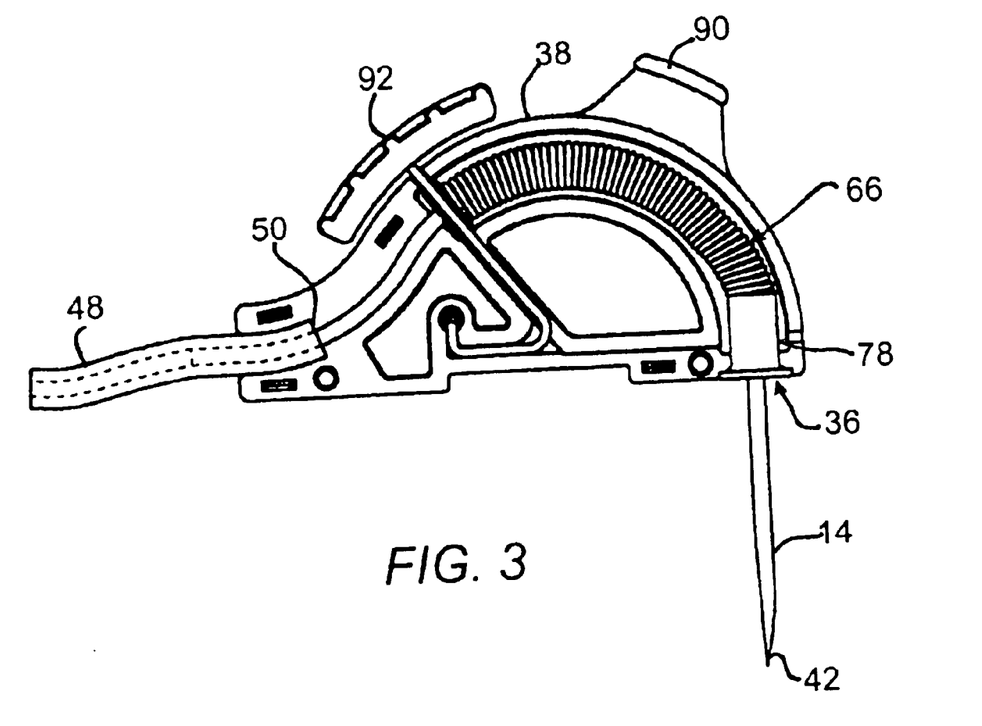
FIG. 3 is a side cross-sectional view of the safety needle device of FIG. 1 illustrating the manner in which a sheath assembly is retracted within its needle housing.

FIGS. 2 and 3 show a proximal needle portion 44 of the needle 16. The proximal needle portion 44 is exposed outside of the needle housing 19 by extending through a proximal opening 46 thereof. This needle portion 44 is connected to a flexible infusion tube or tubing 48, in one end 50 of which is rigidly connected to the needle housing 18 through its proximal opening 46. The other end (not shown) of the infusion tubing is typically placed in communication with a conventional syringe or an infusion pump (not shown).

Referring specifically to FIGS. 9a and 9b, needle-retaining projections 52 are preferably formed adjacent the proximal opening 46. These projections 52 provide an interference and mechanical lock on the tubing 48 when the two housing halves 20, 22 are assembled. Moreover, the portion of the needle 16 which lies between the groove 34 and the proximal opening 46 may be secured in place through the use of a fitting track 54 or adhesive.

Figure 7A:
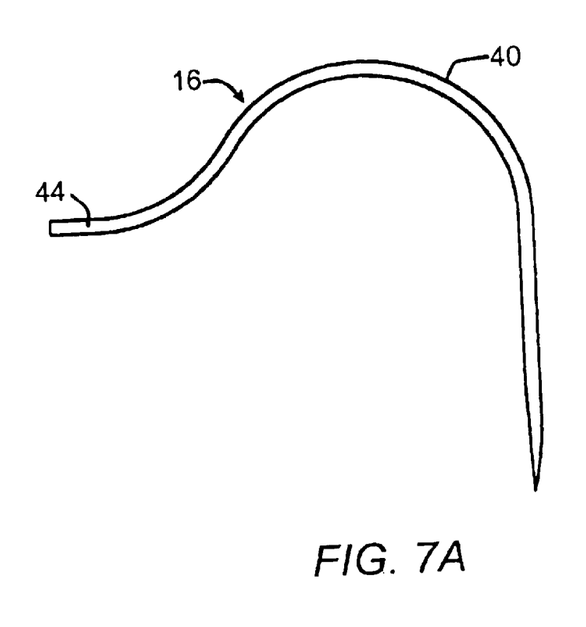
FIG. 7a is a side view of a needle having a bent intermediate portion which corresponds to the configuration of an elongate groove formed within the needle housing of FIG. 1.
Figure 7B:
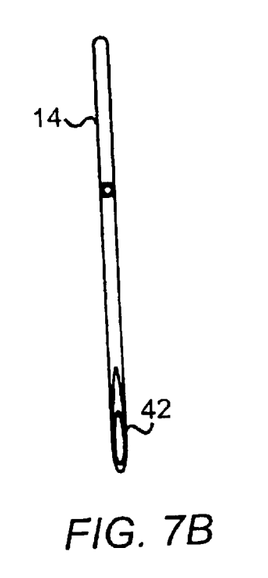
FIG. 7b is a partial side view of the needle of FIG. 7a and illustrating its distal portion which defines a non-coring pointed end.

As shown in FIGS. 3 and 7a–7b, a distal needle portion 14 is provided generally opposite to the proximal needle portion 44. The distal needle portion 14 is exposed outside of the needle housing 18 extending downwardly through the distal housing opening 36. As briefly mentioned above, this portion 14 forms a needle point 42 at its exposed end which is used for penetrating the patient's skin and accessing the implanted subcutaneous IV port.

Referring now to FIGS. 1, 2, 6a and 11, the needle housing 18 has a lower housing surface 56 which defines a recess 58 underneath. This lower housing recess 58 is utilized for accommodating a hold-down platform 60. More specifically, the hold-down platform 60 is maintained within the recess 58 by various conventional attachment means (i.e., adhesive, fasteners, or the like).

The hold-down platform 60 features at least two platform strips 62 which radially extend out from the needle housing 18. In this respect, the platform strips 62 are disposed in a manner as to form a generally perpendicular relationship with the distal needle portion 14. The hold-down platform 60 is primarily used to secure the safety needle device 10 upon the patient while infusion takes place by means of taping over the platform strips 62 and the patient's skin. The platform 60 may be fabricated from any rigid or semi-rigid material such as plastic or rubber. In one configuration, the hold-down platform 60 is formed having a generally circular configuration (best shown in FIG. 11). In the other configurations, it is formed having a generally rectangular configuration (best shown in FIG. 1).

Figure 10:
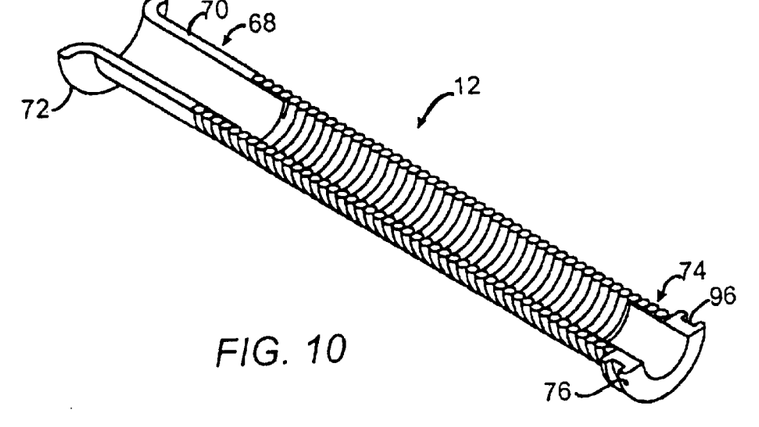
FIG. 10 is a perspective cross-sectional view of the sheath assembly of FIGS. 2 and 3 illustrating its proximal and distal tip components.

FIGS. 2, 3 and 10–12 depict an elongate sheath assembly 64 and illustrates its ability to move from within to and out of the needle housing 18. In particular, the elongate sheath assembly 64 is disposed in a retracted position designated by the numeral 66 within the internal groove 34 of the needle housing 18 in a manner as to surround the intermediate needle portion 40. The assembly 64 has a longitudinal length that is substantially equal or somewhat longer than the arcuate length of the internal groove 34. Obviously, the sheath assembly 64 has a diameter which is less than that of the groove 34 so as to allow its axial movement therewithin. Although the sheath assembly 64 may be formed from various materials, it is preferably made-from an elongated wound wire constructed of stainless steel (as shown in FIG. 10).

The sheath assembly 64 includes a distal end 68 which mounts to a distal tip component 70. Preferably, the distal tip component 70 is fabricated from a plastic, preferably transparent, material. However, the distal tip component 70 should in no way be limited to such construction as other forms of rigid or semi-rigid tips (e.g., metal or rubber tips) may be used in lieu thereof. The distal tip component 70 is attached to the distal sheath end 68 either through the process of insert molding or adhesive. The tip component 70 may include a distal tip 72 having a diameter size generally greater than that of the groove's distal opening 78, but substantially equal to or lesser than the diameter of the distal housing opening 36 (as shown in FIG. 3). Alternatively, the diameter of the distal tip 72 may be sized to be somewhat similar to the diameter of the distal groove opening 78 (as shown in FIG. 11).

The sheath assembly 64 further includes a proximal sheath end 74 which is located generally opposite to the distal sheath end 68. A proximal tip component 76 is attached to the proximal sheath end 74. Similar to the distal tip component 70, the proximal tip component 76 can be attached via insert molding or adhesive. The tip component 76 has a diameter size which is generally greater than the diameter of the groove's distal opening 78. Such diameter size of the proximal tip component 76 facilitates stopping the sheath assembly 64 once it has reached its fully extended position designated generally by the numeral 80 (i.e., the distal tip component 70 being advanced over and beyond the distal needle point 42 while enclosing the distal needle portion 14 with the sheath assembly 64). Although other types of tip components may be used, the proximal tip component 76 is preferably fabricated as a stainless steel or plastic ferrule.

Referring now to FIGS. 2, 3, 8a–8c and 12, the needle housing 18 includes a biasing member 82 therewithin. This biasing member 82 is secured in place within its allocated track 84 which prevents it from bending. A blind hole 86 is also provided as a further insurance in securing the biasing member 82. Cored-out pockets 88 are defined about the biasing member 82 in order to maintain a constant wall thickness. A top projection 90 is also provided on each of the housing halves 20, 22 to resist squeezing the track 84 together and to prevent the free movement of the biasing member 82 when removing the needle 16 from the patient. The biasing member 82 is used for moving the sheath assembly 64 along the groove 34 between the retracted and extended positions 66, 80. This can be accomplished through its engagement to the proximal tip component 76 and to an outwardly exposed knob member 92.

The knob member 92 is provided external to the needle housing 18 and allows the user to manually and passively control the movement of the sheath assembly 64 along the elongated internal groove 34.

More specifically, an extension 94 of the biasing member 82 is connected to a recess 96 (shown in FIG. 10) formed on the proximal tip component 76. The biasing member's extension 94 forms a circular bend portion 95 which extends around the proximal tip component's recess 96. The extension 94 further extends out and attaches to the knob member 92 via insert molding or adhesive. Due to the torsional spring property of biasing member 82 which naturally urges the sheath assembly 64 toward the extended position 80, the user may utilize the knob member 92 to control the sheath assembly 64 when passively moving from its retracted to extended position.

Figure 8A:
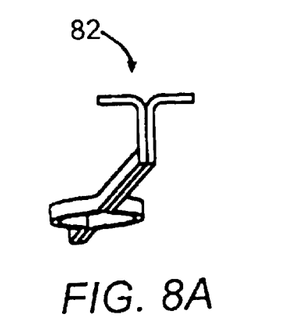
FIG. 8a is a front perspective view of a torsional arm which is used for moving the sheath assembly of FIGS. 2 and 3 between the retracted and extended positions.
Figure 8B:
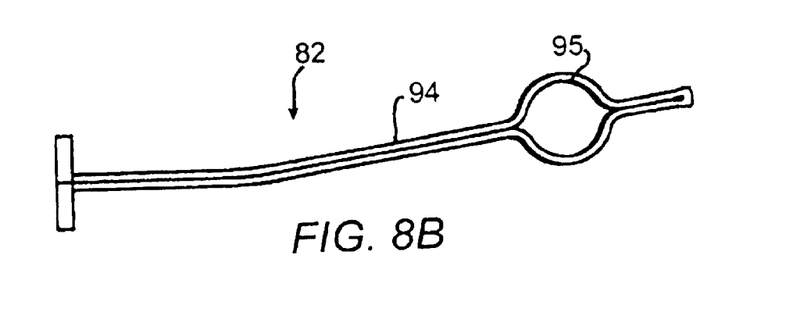
FIG. 8b is a top view of the torsional arm of FIG. 8a and illustrating the direction in which it bends when being inserted within proximal and distal notches of the needle housing.
Figure 8C:
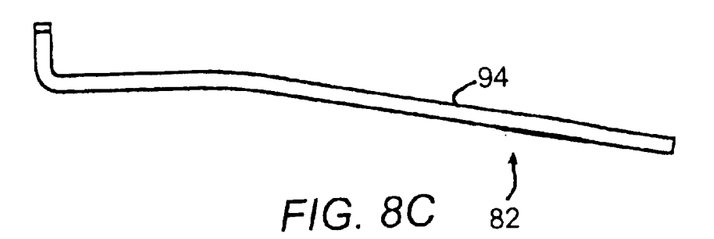
FIG. 8c is a side view of the torsional arm of FIG. 8a illustrating the direction in which it bends when the sheath assembly is moved between the retracted and extended positions.

The biasing member 82 is preferably fabricated from a resilient material such as stainless spring steel or Nitinol. Due to such elastic nature, the extension 94 of the biasing member 82 is capable of bending vertically when the sheath assembly 64 is moved between the retracted and extended positions 66, 80 (best shown in FIG. 8c). As illustrated in FIG. 8b, it can even bend sideways when the extension 94 is snapped into the proximal notch 98 (for maintaining the retracted position 66) or into the distal notch 100 (for maintaining the extended position 80). The biasing member 82 used with the present safety needle device 10 can take the form of a torsional arm or a torsional spring.

Figure 13:
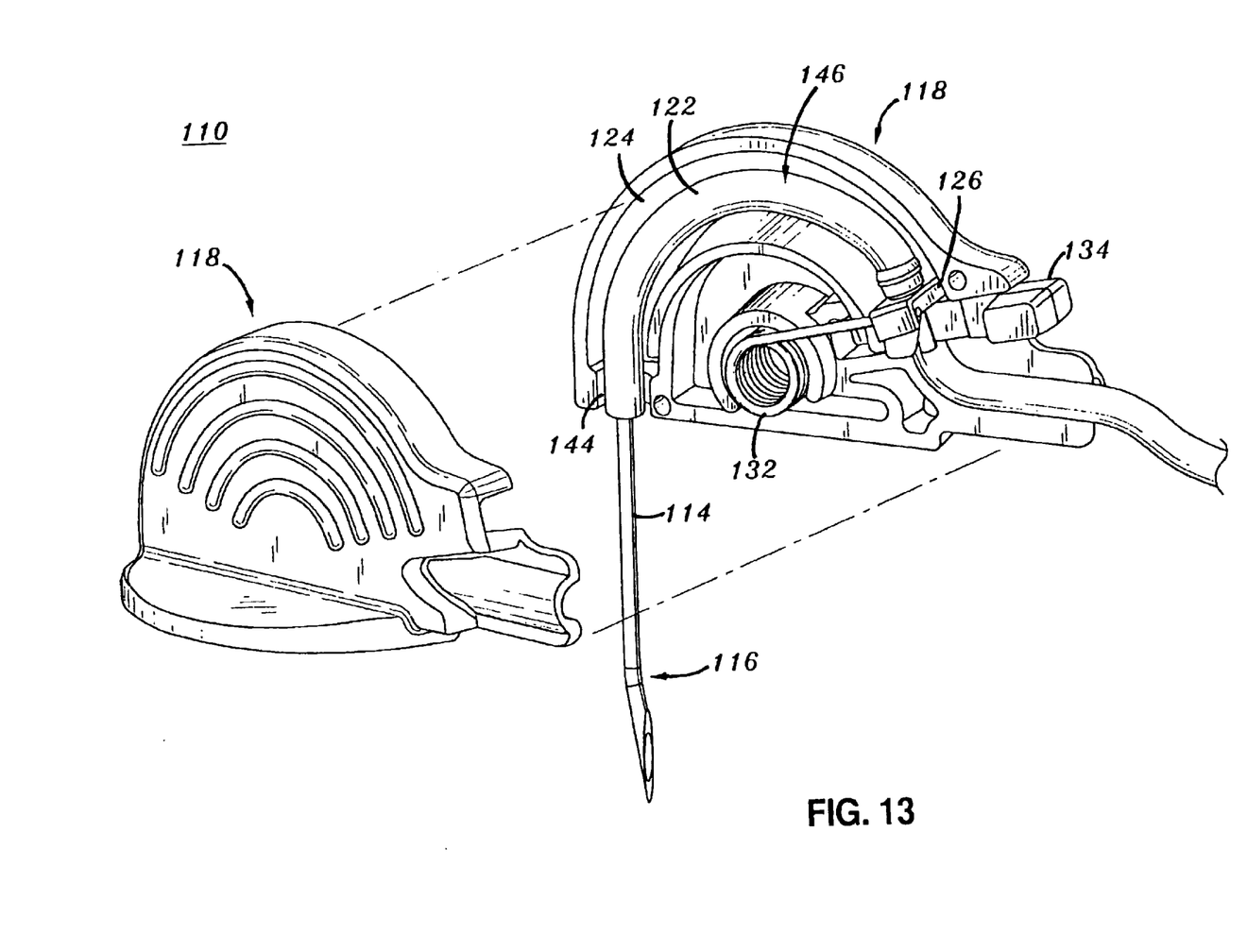
FIG. 13 is an exploded perspective view of a safety needle device constructed in accordance with an alternate embodiment of the present invention and illustrating its needle housing having generally half-circular platform strips extending outwardly therefrom.
Figure 16:
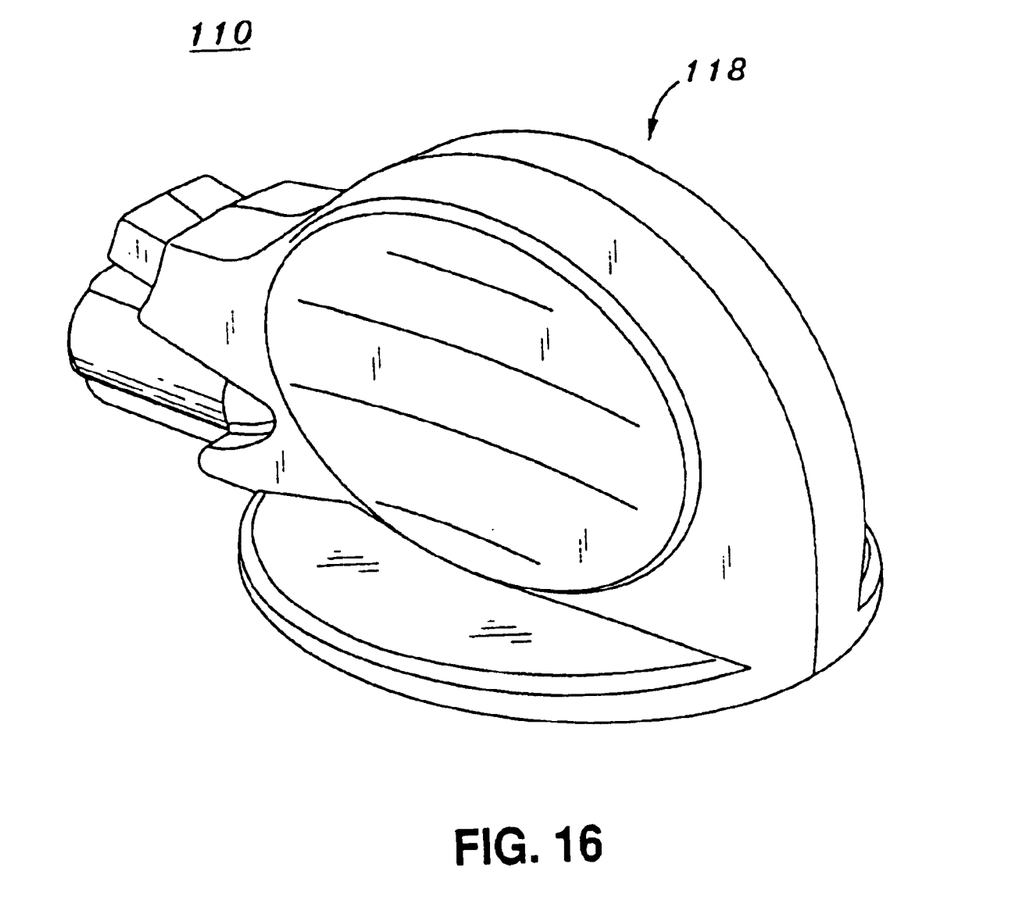
FIG. 16 is a perspective view of the safety needle device of FIG. 13 and illustrating its needle housing which portrays an alternate outer configuration than the one shown in FIG. 13.

Referring now to FIGS. 13 and 16, there is shown a passive safety needle device 110 which is constructed in accordance with an alternate embodiment of the present invention. The alternately embodied safety needle device 110 is essentially designed to perform the same function as that of the above-described needle device 10, that is, to passively extend its sheath assembly 122 over the distal portion 114 of the needle 116 (i.e., Huber needle), and hence provide effective protection against dangers of needle-stick injuries. However, it accomplishes such objective through a structural configuration which is somewhat different than the one disclosed above.

First, although the safety needle device 110 of the alternate embodiment may utilize a similar or identical needle housing 18 as described above, it may alternatively display its own unique type of needle housing 118 which is aesthetically different therefrom. Such needle housing 118 is exemplified in FIG. 16 and as can be seen from that figure, its outer shape or configuration is substantially similar as its counterpart shown in FIG. 11. One major difference between them, however, is that the needle housing 118 of FIG. 16 eliminates the need for any finger-graspable projections 30 and rather provides a substantially continuous and smooth outer surface in lieu thereof. Furthermore, the needle housing 118 is preferably fabricated from a plastic material and may optionally characterize a transparent or semi-transparent body.

Figure 14:
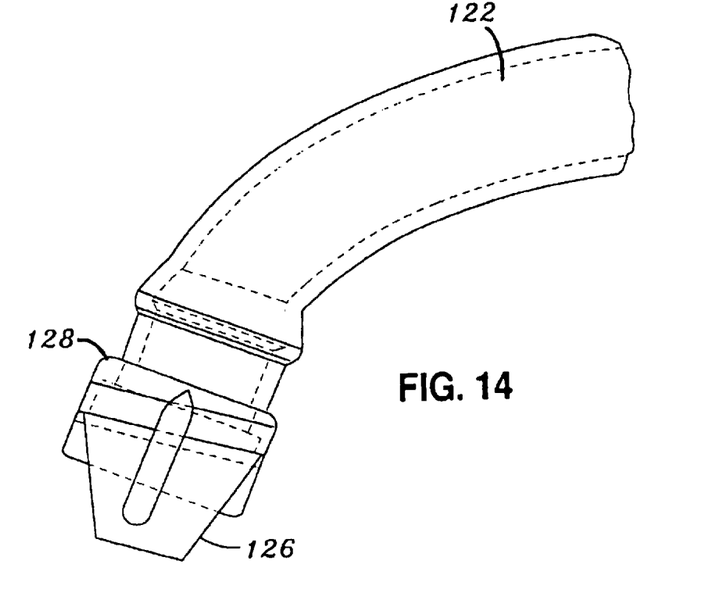
FIG. 14 is a side view of the safety needle device of FIG. 13 and illustrating the manner in which its tip body is barb fitted through an end of the sheath assembly.
Figure 15:
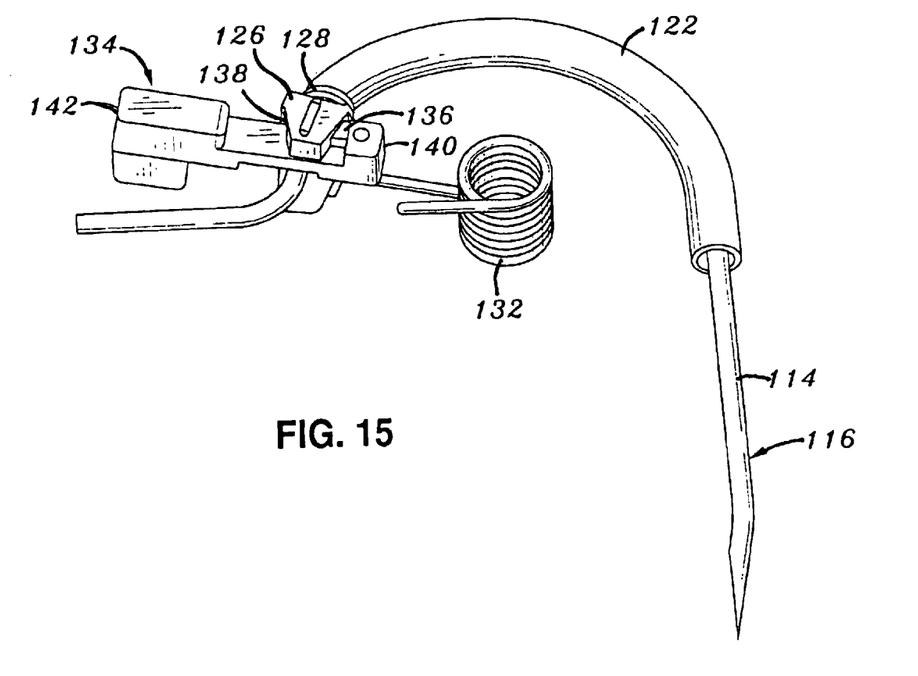
FIG. 15 is a perspective view of the safety needle device of FIG. 13 and illustrating its trigger member which retains the tip body and the sheath assembly in a retracted position.

As illustrated in FIGS. 14 and 15, the safety needle device 110 of the alternate embodiment additionally utilizes a different type of proximal tip component 126 for passively moving the sheath assembly 122 out of the groove 124 and over the needle 116. Instead of using a ferrule as the proximal tip component 76, the alternative safety needle device 110 utilizes a specially manufactured tip body 126 in its place (best shown in FIG. 15). Although this tip body 126 may be fabricated from any rigid material, it is preferably made through plastic molding.

The tip body 126 is attached to the sheath assembly 122 at its proximal sheath end 128. It is contemplated herein that the tip body 126 may become attached to the proximal sheath end 128 by various methods of attachment such as fastening or adhering. Preferably, however, the tip body 126 is attached through barb fitting method. More particularly, the tip body 126 defines a tip protrusion 130 which is extended through and pressed into the proximal sheath end 128 of the sheath assembly 122. Such barb fitting of the tip protrusion 130 into the proximal sheath end enables the tip body 126 to be securely affixed to the sheath assembly 122 thereat. This in turn allows the sheath assembly 122 to passively transition along the groove 124 and be deployed outside of the needle housing 118 when the tip body 126 is caused to move in that direction by the biasing member 132 that it is connected to. Although other types of biasing members 132 such as a torsional arm may be utilized for this purpose, it is preferred that a torsional spring is used as the biasing member 132 of the alternately embodied safety needle device 110 (shown in FIG. 15).

The specially manufactured tip body 126 is releasibly mounted upon a trigger member 134 which is specifically designed for the purpose of retaining and releasing the tip body 126. In order to accomplish such objective, the trigger member 134 possesses a structural configuration which is sufficient to be elongated from within the needle housing 118 to the outside thereof. Although the trigger member 134 may be variously configured and/or shaped, it is preferably elongated in a bar-like configuration. Such configuration of the trigger member 134 facilitates in maintaining the tip body 126 in place against the spring force applied by the biasing member 132.

More specifically, the trigger member 134 includes a tip retaining projection 136 which is adapted to engage an opening 138 formed through the tip body 126. This projection 136 is formed adjacent an inner end 140 of the trigger member 134 which is disposed within the needle housing 118. The tip retaining projection 136 extends from about the inner end 140 of the trigger member 134 towards an outer end 142 thereof where it engages the opening 138 of the tip body 126 mounted therebetween.

As briefly mentioned above, the outer end 142 of the trigger member 134 is exposed through the needle housing 118 and serves as a trigger mechanism for moving the tip body 126 toward the distal opening 144 of the groove 124. Due to its barb fitting arrangement with the sheath assembly 122, the movement of the tip body 126 effectuates the passive movement of the sheath assembly 122 from the retracted position 146 to the extended position (not shown).

The manner of repositioning the sheath assembly 122 to the extended position is accomplished through the release of the tip body 126 from the trigger member 134. Essentially, the tip retaining projection 136 of the trigger member 134 maintains the tip body 126 and the sheath assembly 122 in the retracted position 146 until the tip body 126 is manually released from the trigger member 134. This automatically triggers the tip body 126 and the sheath assembly 122 to move towards the extended position. Such release of the tip body 126 is performed by manually pushing in the outer end 142 of the trigger member 134 towards the needle housing 118. This causes the tip retaining projection 136 to slip out from the opening 138 and free the tip body 126 from its holding.

Because the biasing member 132 is mechanically connected to the tip body 126 to apply a spring force toward the distal opening 144 of the groove 124, the tip body 126 is automatically caused by the biasing member 132 to be urged in that direction and form the extended position. Due to its barb fitting connection with the proximal sheath end 128, the tip body 126 pushes the sheath assembly 122 towards the distal opening 144 of the groove 124. This effectuates the sheath assembly 122 to be passively deployed outside of the needle housing 118 and form the extended position with respect to the distal portion 114 of the needle 116.

Similar to the above-described proximal tip component 76, the tip body 126 possesses a body size which is substantially larger than the distal opening 144 of the groove 124. Because of its larger body size, the tip body 126 is forced to stop once it reaches and abuts the portion of the groove 124 which converges inwardly to narrow the distal opening 144 thereof. However, the size of the distal opening 144 is sufficiently large enough to allow the sheath assembly 122 to pass therethrough and be deployed outside of the needle housing 118 to extend over the entirety of the distal needle portion 114. The sheath assembly 122 remains in this outwardly deployed configuration as the spring force of the biasing member 132 continuously urges the tip body 126 against the converged portion of the groove 124 which forms its narrowed distal opening 144.

With the structure defined, the operation of the safety needle device 10 of the first embodiment is described herein to essentially illustrate the operation of the safety needle device 110 of the second embodiment as well. The safety needle device 10 of the first embodiment is designed for the purpose of protecting a user from getting stuck when withdrawing the needle 16 from the patient. Initially, a user grabs the exterior of the housing having the distal needle point extending downwardly therefrom. The distal needle point 42 is then inserted into a designated skin area of the patient to access the implanted IV port. By such penetration, various tasks such as delivering fluids and medications, drawing blood for diagnostic testing and/or infusing blood products may be conducted. Optionally, the safety needle device 10 of the present invention can be secured in place by taping its radially extending platform strips 62 to the patient's surrounding skin area.

After performing any one of the tasks as described above, the needle 16 is withdrawn from the patient. While withdrawing the needle 16, the externally disposed knob member 92 is manipulated by the user to manually control the outward deployment of the sheath assembly 64 from its retracted position 66 to its extended position 68. Such movement is further facilitated by the torsional spring 82. When the sheath assembly 64 travels to its extended position 68, the sheath surrounds and covers the distal needle portion and needle tip thereby preventing any inadvertent needle stick to the user. In the case of the second embodied safety needle device of the second embodiment, the outward deployment of the sheath assembly 122 can take place by the manual pressing of the trigger member 134 which automatically triggers such deployment to occur.

The safety needle device 10 of the present invention is then ready for proper disposal. Preferably, the used safety needle device 10 is thrown away in a Sharps container which is designated for used medical devices.

Additional modifications and improvements of the present invention may also be apparent to those of ordinary skill in the art. Thus, the particular combination of parts described and illustrated herein is intended to represent only certain embodiments of the present invention, and is not intended to serve as limitations of alternative devices within the spirit and scope of the invention.

What is claimed is:

1. A safety needle device for protecting a user against a needle-stick injury, the needle device comprising:
   a needle housing having a distal housing opening and an internal arcuate groove formed within the needle housing and extending to the distal housing opening;
   a needle disposed within the arcuate groove and having a distal needle portion extending away therefrom through the distal housing opening;
   an elongate sheath assembly surrounding the needle and being moveable along the arcuate groove;
   a torsional spring disposed within the needle housing and being sized and configured to apply a force upon the sheath assembly for transition thereof towards and out of the distal housing opening; and
   a trigger member retaining the sheath assembly within the needle housing against the force urging the sheath assembly towards the distal housing opening, wherein the trigger member is sized and configured to release the sheath assembly from retention to allow the sheath assembly to transition towards and out of the distal housing opening via the force to thereby enclose the distal needle portion therewith and protect the user against the needle stick injury.

2. The needle device of claim 1 wherein the needle housing is fabricated from a plastic material.

3. The needle device of claim 1 wherein the needle housing is fabricated from a semi-transparent material.

4. The needle device of claim 1 wherein the needle housing comprises a lower housing surface having a hold-down platform extending outwardly therefrom.

5. The needle device of claim 4 wherein the hold-down platform has a generally circular configuration.

6. The needle device of claim 1 wherein the needle housing comprises a groove elongated therewithin and communicating with the distal housing opening, the sheath assembly surrounding the needle within the groove.

7. The needle device of claim 1 further comprising a tip body and wherein the sheath assembly has a proximal sheath end, the tip body being engaged between the proximal sheath end and the torsional spring.

8. The needle device of claim 7 wherein the tip body is fabricated from a plastic material.

9. The needle device of claim 7 wherein the tip body has a tip protrusion extending toward and engaging the proximal sheath end.

10. The needle device of 9 the tip protrusion is securely fitted through the proximal sheath end.

11. The needle device of claim 7 wherein the tip body has an opening and the trigger member includes an inner end having a tip retaining projection formed adjacent thereto, the tip retaining projection being sized and configured to extend into the opening and retain the tip body in place therewith.

12. The needle device of claim 11 wherein the tip retaining projection is sized and configured to disengage from the opening and release the tip body from retention so as to allow the sheath assembly to transition toward the distal housing opening via the force of the torsional spring.

13. The needle device of claim 12 wherein the trigger member includes an outer end exposed through the needle housing for actuating the disengagement of the tip retaining projection from the opening of the tip body.

14. The needle device of claim 13 wherein the exposed outer end of the trigger member is manually pressed toward the needle housing to actuate the disengagement of the tip retaining projection from the opening of the tip body.

15. The needle device of claim 1 wherein the trigger member is fabricated from a plastic material.

16. The needle device of claim 1 wherein the sheath assembly is fabricated from a polymer material.

17. The needle device of claim 16 wherein the polymer material is a semi-rigid polymer material.

18. The needle device of claim 1 wherein the needle is a Huber needle.

19. A safety needle device for protecting a user against a needle-stick injury, the needle device comprising:

a needle housing having a distal housing opening and an internal arcuate groove formed within the needle housing, the arcuate groove initiating intermediate the needle housing and extending to the distal housing opening;

a needle having an intermediate portion and a distal needle portion, the intermediate portion being disposed within the arcuate groove and being formed complementary thereto, the distal needle portion extending out of the distal housing opening;

an elongate sheath assembly surrounding the needle and being moveable along the arcuate groove;

a torsional spring disposed within the arcuate groove and being sized and configured to apply a force upon the sheath assembly for transition thereof towards and out of the distal housing opening; and a trigger member retaining the sheath assembly within the needle housing against the force urging the sheath assembly towards the distal housing opening, wherein the trigger member is sized and configured to release the sheath assembly from retention to allow the sheath assembly to transition towards and out of the distal housing opening via the force to thereby enclose the distal needle portion therewith and protect the user against the needle stick injury.

20. The safety needle device of claim 19 wherein:

the needle housing has generally planar opposing sides interconnected by an arcuately shaped upper housing surface;

the arcuate groove and the upper housing surface having complementary bend radii.

21. The safety needle device of claim 20 wherein at least one of the sides has finger-graspable projections formed thereon for facilitating handling of the safety needle device.

* * * * *